United States Patent
Pang

(10) Patent No.: US 11,303,645 B2
(45) Date of Patent: Apr. 12, 2022

(54) ONLINE DIAGNOSTIC PLATFORM, AND PERMISSION MANAGEMENT METHOD AND PERMISSION MANAGEMENT SYSTEM THEREOF

(71) Applicant: AUTEL INTELLIGENT TECHNOLOGY CORP., LTD., Guangdong (CN)

(72) Inventor: Shengsheng Pang, Guangdon (CN)

(73) Assignee: AUTEL INTELLIGENT TECHNOLOGY CORP., LTD., Shenzhen (CN)

( * ) Notice: Subject to any disclaimer, the term of this patent is extended or adjusted under 35 U.S.C. 154(b) by 0 days.

(21) Appl. No.: 17/140,747

(22) Filed: Jan. 4, 2021

(65) Prior Publication Data

US 2021/0126918 A1    Apr. 29, 2021

Related U.S. Application Data

(63) Continuation of application No. PCT/CN2020/070486, filed on Jan. 6, 2020.

(30) Foreign Application Priority Data

Jan. 15, 2019 (CN) .......................... 201910036464.0

(51) Int. Cl.
*G06F 15/173* (2006.01)
*H04L 29/06* (2006.01)
(Continued)

(52) U.S. Cl.
CPC ............ *H04L 63/102* (2013.01); *H04L 41/22* (2013.01); *H04L 63/105* (2013.01); *H04L 63/20* (2013.01); *H04L 67/02* (2013.01)

(58) Field of Classification Search
CPC ....... G16H 80/00; H04L 41/22; H04L 63/102; H04L 63/104; H04L 63/105; H04L 63/20; H04L 67/02; H04L 67/306
(Continued)

(56) References Cited

U.S. PATENT DOCUMENTS

2015/0156251 A1   6/2015  Zhou
2015/0180894 A1*  6/2015  Sadovsky ............... H04L 67/22
                                                            726/22
(Continued)

FOREIGN PATENT DOCUMENTS

CN    103001803 A      3/2013
CN    104050401 A  *   9/2014
(Continued)

OTHER PUBLICATIONS

International Search Report dated Mar. 13, 2020; PCT/CN2019/129877.
(Continued)

*Primary Examiner* — Liang Che A Wang

(57) ABSTRACT

The present invention relates to an online diagnostic platform, and a permission management method and a permission management system thereof. The permission management method includes: when user information of a registered user is received, assigning a role in a role set to the registered user; determining a permission corresponding to the role; and generating a menu corresponding to the registered user, where the menu includes one or more function portals, the function portal being used for requesting execution of a diagnostic service function. The method uses security control policies such as the registered user, the role and the permission, and is flexible in management and relationship configuration. In addition, the permission management system is separated from a service system, has good expansi-
(Continued)

bility, and can ensure stable running and data security of the system.

14 Claims, 6 Drawing Sheets

(51) Int. Cl.
 *H04L 41/22* (2022.01)
 *H04L 67/02* (2022.01)
(58) Field of Classification Search
 USPC .................................... 709/223, 226; 726/1
 See application file for complete search history.

(56) References Cited

U.S. PATENT DOCUMENTS

| | | | | |
|---|---|---|---|---|
| 2015/0200950 | A1* | 7/2015 | Meunier | G06Q 20/40 |
| | | | | 705/35 |
| 2018/0091516 | A1* | 3/2018 | Nixon | H04L 63/20 |
| 2021/0126918 | A1 | 4/2021 | Pang | |

FOREIGN PATENT DOCUMENTS

| | | | |
|---|---|---|---|
| CN | 104050401 A | | 9/2014 |
| CN | 104360846 A | * | 2/2015 |
| CN | 104360846 A | | 2/2015 |
| CN | 104462888 A | | 3/2015 |
| CN | 105303084 A | | 2/2016 |
| CN | 107491858 A | | 12/2017 |
| CN | 108009407 A | | 5/2018 |
| CN | 108196837 A | | 6/2018 |
| CN | 108268024 A | | 7/2018 |
| CN | 108600177 A | | 9/2018 |
| CN | 109817347 A | | 5/2019 |

OTHER PUBLICATIONS

The First Chinese Office Action dated Apr. 23, 2020; Appln. No. 201811639171.3.

\* cited by examiner

ONLINE DIAGNOSTIC PLATFORM, AND PERMISSION MANAGEMENT METHOD AND PERMISSION MANAGEMENT SYSTEM THEREOF

This application is a continuation application of International Application No. PCT/CN2020/070486, filed on Jan. 6, 2020, which claims priority of Chinese Patent Application No. 201910036464.0, filed on Jan. 15, 2019, which is incorporated herein by reference in its entirety.

BACKGROUND

Technical Field

This application relates to the field of cloud network technologies, and in particular, to an online diagnostic platform, and a permission management method and a permission management system thereof.

Related Art

With the continuous development of the Internet and the continuous progress of wireless communications technologies, cloud technologies begin to be widely applied to many different industries. An automobile diagnosis industry gradually moves from offline diagnosis to online diagnosis.

Such an online diagnostic platform or online diagnostic platform has good flexibility and it is convenient to implement centralized management and statistics of data. Each user may also conveniently execute, through the online diagnostic platform, service functions required by the user.

The online diagnostic platform or system constructed by using Internet technologies brings convenience, but also leads to data security and privacy problems. Therefore, to ensure the security of the entire online diagnostic platform, a perfect permission management system is necessary.

However, with the continuous expansion of a quantity of users and the continuous iterative update of the system, a security control policy of the existing permission management system has problems that permission management is not flexible enough, the management is complex, the subsequent function expansion of the system is not facilitated and the like. Consequently, it is easy to generate potential safety hazards such as attacks from uniform resource locator (URL) intrusion, structured query language (SQL) injection and the like.

SUMMARY

Embodiments of the present invention aim to provide an online diagnostic platform, and a permission management method and a permission management system thereof that can resolve the problems of complex permission management and poor flexibility.

To resolve the foregoing technical problems, the embodiments of the present invention further provide the following technical solution:

a permission management method. The permission management method includes: when user information of a registered user is received, assigning a role in a role set to the registered user; determining a permission corresponding to the role; and generating a menu corresponding to the registered user, where the menu includes one or more function portals, the function portal being used for requesting execution of a diagnostic service function.

In some embodiments, the step of generating a menu corresponding to the registered user includes:
determining a user attribute of the registered user, where the user attribute includes a front-end user and a back-end user;
generating a corresponding first menu when the user attribute is the front-end user; and generating a corresponding second menu when the user attribute is the back-end user.

In some embodiments, the first menu is a fixed menu and the second menu is a dynamic menu that changes with the permission of the registered user.

In some embodiments, the step of generating a corresponding second menu when the user attribute is the back-end user specifically includes:
obtaining the permission of the registered user; determining a function portal corresponding to each permission; and integrating all function portals corresponding to the permission of the registered user to form the second menu.

In some embodiments, the back-end user includes a system administrator and an operator.

The step of assigning one or more roles in the role set to the registered user to enable the registered user to have the corresponding permission specifically includes:
assigning a role to the registered user when the user attribute of the registered user is the front-end user or the system administrator; and
assigning one or more roles to the registered user when the user attribute of the registered user is the operator.

In some embodiments, the permission is a set including one or more interfaces, so that a function of an online diagnostic platform corresponding to the interface is allowed to be used.

In some embodiments, the method further includes:
determining, through the menu, a function requested to be executed by the registered user; and
verifying whether the registered user has a permission corresponding to the function requested to be executed;
allowing to execute the function if yes; and
refusing to execute the function if no.

To resolve the foregoing technical problems, the embodiments of the present invention further provide the following technical solution a permission management system.

The permission management system includes: a user management module, configured to, when user information of a registered user is received, assign a role in a role set to the registered user; a permission management module, configured to determine a permission corresponding to the role; and a menu module, configured to generate a menu corresponding to the registered user, where the menu includes one or more function portals, the function portal being used for requesting execution of a diagnostic service function.

In some embodiments, the menu module specifically includes: an attribute determination unit, a first menu generation unit and a second menu generation unit, where the attribute determination unit is configured to determine a user attribute of the registered user, and the user attribute includes a front-end user and a back-end user;
the first menu generation unit is configured to generate a corresponding first menu when the user attribute is the front-end user; and
the second menu generation unit is configured to generate a corresponding second menu when the user attribute is the back-end user.

In some embodiments, the first menu is a fixed menu and the second menu is a dynamic menu that changes with the permission of the registered user.

In some embodiments, the second menu generation unit is specifically configured to: obtain the permission of the registered user; determine a function portal corresponding to each permission; and integrate all function portals corresponding to the permission of the registered user to form the second menu.

In some embodiments, the back-end user includes a system administrator and an operator. The user management module is specifically configured to: assign a role to the registered user when the user attribute of the registered user is the front-end user or the system administrator; and assign one or more roles to the registered user when the user attribute of the registered user is the operator.

In some embodiments, a server further includes a permission module. The permission module is configured to add, delete or edit any permission, and each permission includes a set of one or more interfaces, so that a function of an online diagnostic platform corresponding to the interface is allowed to be used.

In some embodiments, the server further includes an execution control module. The execution control module is configured to: determine, through the menu, a function requested to be executed by the registered user; and determine, according to the permission of the registered user, whether to execute the function requested to be executed.

To resolve the foregoing technical problems, the embodiments of the present invention further provide the following technical solution: an online diagnostic platform.

The online diagnostic platform includes: a client, configured to receive user information of a registered user and send the user information to a permission management system, where the client is further configured to display a menu generated by the permission management system according to the user information; the permission management system, configured to execute the permission management method described above to manage one or more registered users; and a service system, configured to execute a diagnostic service function according to a request of the client.

Compared with the prior art, the permission management method provided in the embodiments of the present invention uses security control policies such as the registered user, the role and the permission, and is flexible in management and relationship configuration. In addition, the permission management system is separated from a service system, has good expansibility, and can ensure stable running and data security of the system.

BRIEF DESCRIPTION OF THE DRAWINGS

One or more embodiments are described by way of example with reference to the corresponding figures in the accompanying drawings, and the descriptions are not to be construed as limiting the embodiments. Elements in the accompanying drawings that have same reference numerals are represented as similar elements, and unless otherwise particularly stated, the figures in the accompanying drawings are not drawn to scale.

DETAILED DESCRIPTION

For ease of understanding the present invention, the present invention is described below in more detail with reference to the accompanying drawings and specific embodiments. It should be noted that when an element is referred to as being "fixed to" another element, it may be directly on the another element or there may be one or more middle elements between the elements. When an element is referred to as being "connected to" another element, it may be directly connected to the another element or there may be one or more middle elements between the elements. A direction or location relationship indicated by a term "on", "under", "inner", "outer", "bottom" or the like used in this specification is a direction or location relationship shown based on the accompanying drawings, and is intended to only conveniently describe the present invention and simplify the description, but is not intended to indicate or imply that a mentioned apparatus or element needs to have a particular direction and is constructed and operated in the particular direction. Therefore, the direction or location relationship cannot be understood as a limitation on the present invention. In addition, terms such as "first", "second" and "third" are only used for description and cannot be understood as indicating or implying relative importance.

Unless otherwise defined, meanings of all technical and scientific terms used in this specification are the same as those usually understood by a person skilled in the technical field to which the present invention belongs. In this specification, terms used in the specification of the present invention are merely intended to describe the specific embodiments, but are not intended to limit the present invention. A term "and/or" used in this specification includes any combination or all combinations of one or more related listed items.

In addition, technical features involved in different embodiments of the present invention described below may be combined with each other provided that there is no conflict with each other.

Figure 1:
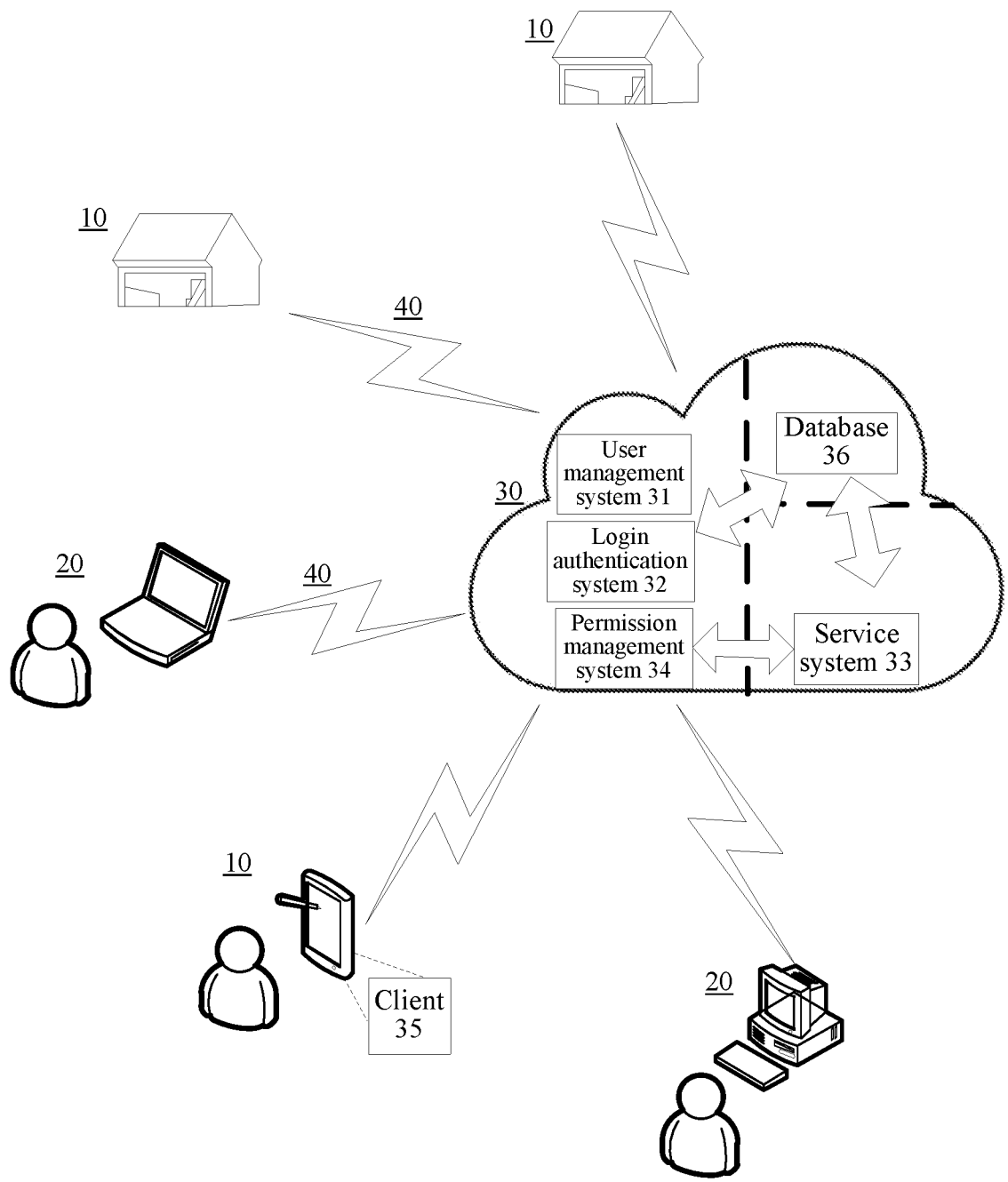
FIG. 1 is a schematic diagram of an application scenario of an online diagnostic platform according to an embodiment of the present invention.

An online diagnostic platform is an electronic platform that is established in a cloud by using Internet technologies and provides corresponding information service functions for various automobile maintenance sites or automobile diagnosis maintenance operators. Based on the online diagnostic platform, the online diagnostic platform may serve as an information interaction medium in the cloud, and is connected to many nodes that are geographically located at different positions, to establish a complete maintenance diagnosis network. FIG. 1 is an example of an application scenario of a maintenance diagnosis network according to an embodiment of the present invention.

As shown in FIG. 1, the entire application scenario includes: a front-end service site 10, a back-end operation site 20, an online diagnostic platform 30, and a communication network 40.

The front-end service site 10 refers to a node that is located at the forefront of equipment maintenance and that provides a real maintenance, diagnosis and repair service, for example, a maintenance shop or a maintenance technician in a maintenance shop. The front-end service site, as a final executor and implementer of the entire maintenance diagnosis network, may be disposed at any geographic position or may be in any form or size.

The back-end operation site 20 is a node that is used for coordinating a plurality of front-end service sites 10, and implementing management of these front-end service sites 10, for example, a personnel department responsible for personnel management of a maintenance technician or a warehousing department responsible for deploying inventory accessories of a maintenance shop. Relative to the front-end service site, the back-end operation site is in back-end operation and management control, and is another type of node in the entire maintenance diagnosis network.

The online diagnostic platform 30 is an electronic computing platform constructed on the basis of a server and a database, can execute corresponding functions such as searching maintenance cases, counting maintenance accidents or annual performance or the like in response to requests sent by various nodes, and is a function and control core of the entire maintenance diagnosis network.

The communication network 40 may be any type of wireless, wired, or combined data transmission network such as a cellular communication network, a Wi-Fi network, or a private local area network. The communication network 40 is used for establishing a communication link between each node (that is, the front-end service site 10 or the back-end operation site 20) and the online diagnostic platform 30 to implement data interaction such as instruction upload and data delivery between the node and the online diagnostic platform.

In the actual use process, the online diagnostic platform 30 usually uses a security control policy for user identity authentication to ensure stable running of the entire maintenance diagnosis network. That is, each of different nodes in the maintenance diagnosis network uses a unique registered user as label or identity information of the node. The node is permitted to use a corresponding function only after steps of identity and permission authentication.

To implement creation and login of the registered user, as shown in FIG. 1, the online diagnostic platform 30 may be provided with a user management system 31 and a login authentication system 32. The user management system 31 creates a new registered user based on a registration behavior of the user. The login authentication system 32 completes the login of the registered user in any type of authentication manner such as an account password or fingerprint recognition.

For example, a maintenance shop may register on the online diagnostic platform and obtain an account number of a registered user and a password through the user management system 31. Then, the account number and the password are used to log in to the online diagnostic platform to request the use of one or more functions of the online diagnostic platform. Finally, the online diagnostic platform determines, according to the permission of the registered user, whether to respond to the request of the registered user and execute the corresponding function.

Figure 9:
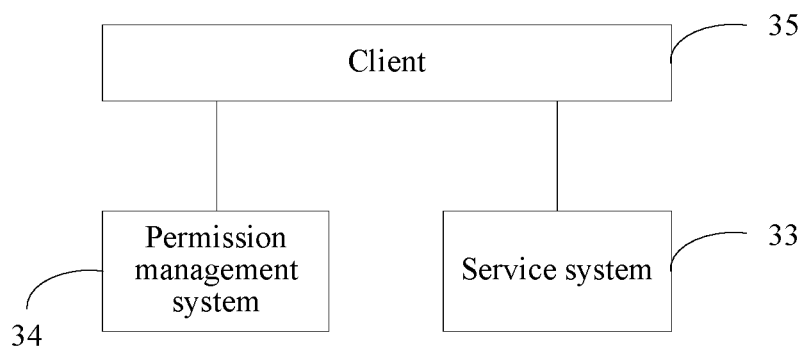
FIG. 9 is a schematic structural diagram of an online diagnostic platform according to an embodiment of the present invention.

Considering that the online diagnostic platform 30 generally requires a plurality of times of iterative version update during use, the functions that the online diagnostic platform 30 can perform are actually in a dynamically changing process. To maintain the expandability of the online diagnostic platform 30 and facilitate completion of functions of the functions, as shown in FIG. 9, main components of the online diagnostic platform 30 may include a service system 33, a permission management system 34 and a client 35.

The service system 33 represents a set of all functions and services that the online diagnostic platform can perform. That is, all service functions and services of the online diagnostic platform are integrated on the service system.

The permission management system 34 is used for managing and verifying the permission of the registered user to determine whether authority is obtained. The service system 33 responds to the request to perform the corresponding service function only after obtaining the authority of the permission management system 34.

The client 35 is a part that interacts with the user. The client may be executed on any type of terminal device, and is configured to receive user information of the registered user and send the user information to the permission management system. In addition, the client displays a menu generated by the permission management system according to the user information.

The online diagnostic platform 30 may further include a database 36 for storing data or instruction information.

The database 36 may be any type of data storage device that can store a program instruction and the data and support searching for the stored data in any storage policy. In some embodiments, the database 36 may be further a distributed storage system.

In this embodiment, the service system 33 and the permission management system 34 may be implemented by using a same hardware device or different hardware devices, or may be implemented by using two mutually independent function modules formed by dividing a same hardware device. The client 35 may be a mobile application or a web page node (that is, log in by inputting a website through a web engine) running on any system (for example, Windows, Android or iOS system).

The online diagnostic platform shown in FIG. 1 and FIG. 9 decouples the service system from the permission management system, so that the service system and the permission management system are independent of each other and do not affect each other. The permission management system 34 prevents "an illegal user" from accessing the system, and restricts the user to access of only an authorized function, thereby ensuring that the online diagnostic platform runs stably and safely without affecting the expansion or update of service functions on the service system 33.

Figure 2:
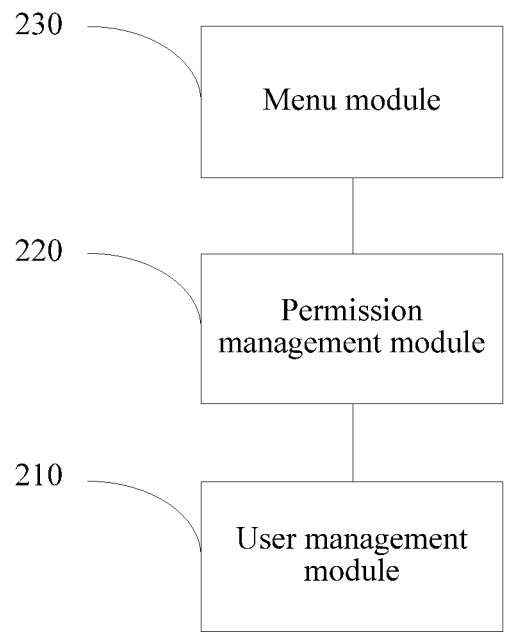
FIG. 2 is a schematic diagram of a permission management system according to an embodiment of the present invention.

As the quantity and complexity of the functions of the online diagnostic platform 30 increase, the permission management system 34 of the online diagnostic platform can implement better and more flexible permission management by using the permission management system provided in this embodiment of the present invention, to obtain convenience in use. FIG. 2 is a functional block diagram of a permission management system according to an embodiment of the present invention.

As shown in FIG. 2, the permission management system includes: a user management module 210, a permission management module 220 and a menu module 230.

There may be a pre-created role set in the permission management system. Based on a role in the role set, the permission management module 220 is configured to assign one or more permissions to the role.

The "role" is a logical concept used for marking a permission set including one or more permissions. The role is constructed as one of levels in the permission management to simplify the operation of permission assignment. For example, the "role" may be a technician or a maintenance shop. The permissions of the technician include access to cases, questioning cases, and sharing (making) cases, and the permissions of the maintenance shop include managing a technician and managing equipment information.

All created roles as elements in the set form the role set. Certainly, the role set may be edited or modified. According to requirements of an actual condition, in some embodiments, editing operations such as deleting and merging may be further performed on existing roles in the role set.

The user management module 210 is configured to assign one or more roles in the role set to the registered user. After a role is assigned to the registered user, the registered user has the permission of the role.

The "registered user" refers to unique identity information that the online diagnostic platform uses to identify or distinguish different nodes. The registered user may be specifically in any appropriate form. For example, the registered user may include an account name and a password, a biometric feature (for example, a fingerprint) or a fixed identification code (for example, a network IP address), or the like provided that a node can be uniquely defined.

The permission refers to authority that may perform some functions. The permission as a safety judgment standard or rule distinguishes actual conditions of different registered users, and prohibits harmful operations to ensure the safe running of the online diagnostic platform.

Preferably, each permission is a set including one or more interfaces through which a function or a service corresponding to the service system is allowed to be invoked. In this way, a mode of refining permission control to an interface hierarchy can basically meet various permission requirements of different users in the actual use process.

The menu module 230 is configured to generate a menu corresponding to the registered user. The "menu" is a combination of one or more function portals. The menu may be displayed on a display screen of a terminal device in any type of form (for example, a list bar), for a user to request the online diagnostic platform to perform the corresponding function.

That is, each function portal corresponds to a function. When the user selects or taps a function portal, the online diagnostic platform receives a request of performing the function.

Figure 3:
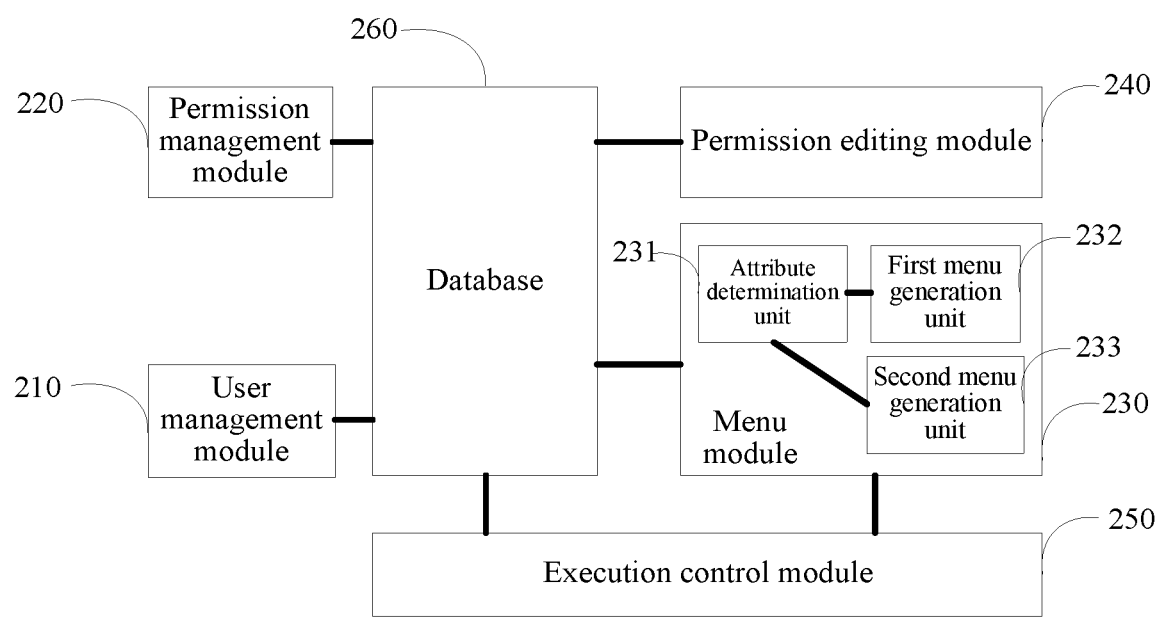
FIG. 3 is a schematic diagram of a permission management system according to another embodiment of the present invention.

Based on the permission definition mode refined to the interface hierarchy, as shown in FIG. 3, compared with the permission management system shown in FIG. 2, the permission management system may further include a permission editing module 240.

The permission editing module 240 is configured to provide editing functions for an interface set, for example, adding, deleting, or editing any permission, for example, adjusting an interface of a permission.

Figure 4:
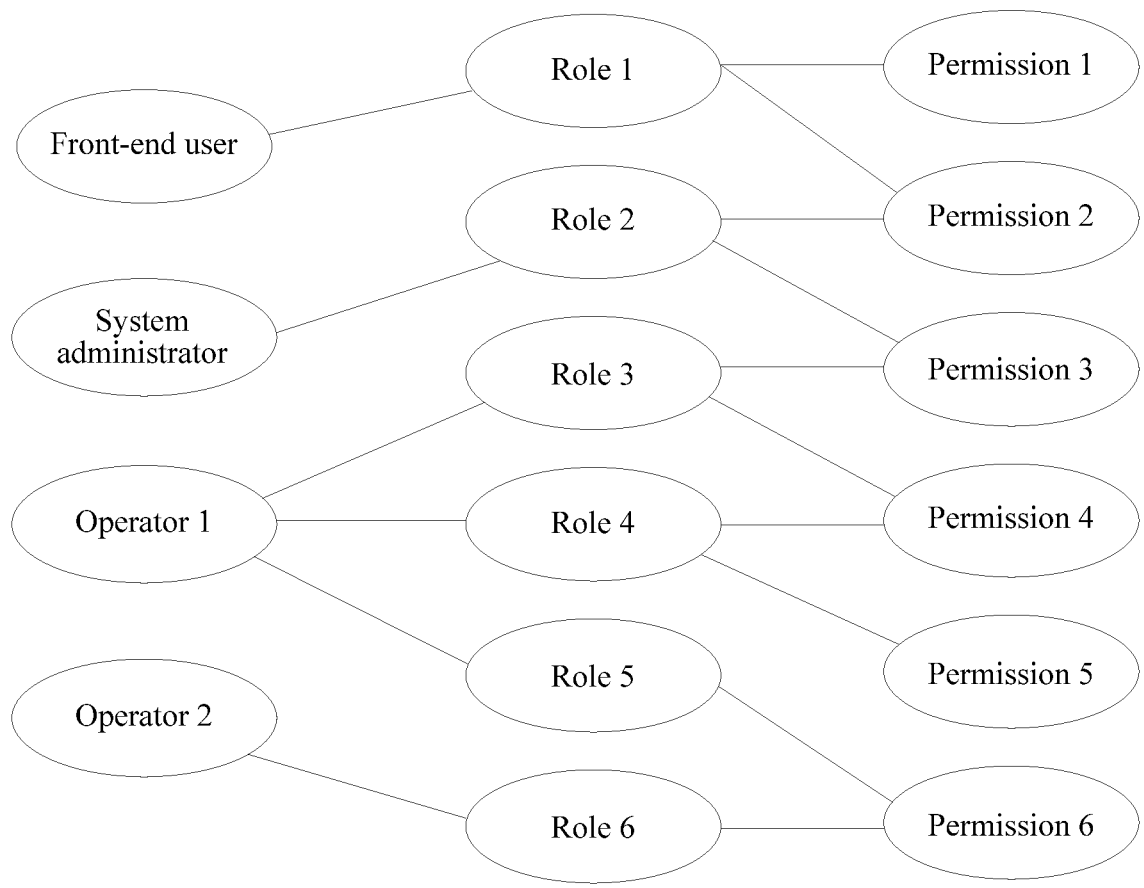
FIG. 4 is a schematic diagram of a hierarchical relationship among a registered user, a role and a permission according to an embodiment of the present invention.

In the permission management system provided in this embodiment, the permission management of the registered user is implemented by assigning the role to the existing registered user and assigning the permission of the role, and a two-level mapping relationship of the registered user-role-permission shown in FIG. 4 may be formed.

The two-level mapping relationship may help simplify the workload of the permission management and improve flexibility of management. For example, when a function is newly added to the online diagnostic platform, a permission of the new function can be simply given to a role through the permission management module 220, so that permission editing of the newly added function can be completed without traversing all registered users.

Still referring to FIG. 1, in an application scenario, each node may be any type of terminal device. The terminal device such as a personal computer, a smartphone, an automobile diagnostic device or a tablet computer includes at least a communication module and an input/output device through which a user joins the communication network 40 and is configured to implement interaction with the user. However, the online diagnostic platform 20 needs to present a corresponding interactive interface to the user on the terminal devices, so that the user can send a request instruction and specify a permission of the user.

Different nodes may belong to different categories. To implement personalized and refined interaction, in some embodiments, as shown in FIG. 3, the menu module 230 specifically includes: an attribute determination unit 231, a first menu generation unit 232 and a second menu generation unit 233.

The attribute determination unit 231 is configured to determine a user attribute of the registered user. The user attribute refers to a type of a node corresponding to the registered user, and may be determined by relevant information submitted during registration and the like.

According to the application scenario shown in FIG. 1, the user attribute may include both a front-end user and a back-end user. The front-end user indicates that the registered user belongs to the front-end service site 10. The back-end user indicates that the registered user belongs to the back-end operation site 20.

Based on a classification result of the attribute determination unit 231, different menus are generated for registered users of different user attributes by using the first menu generation unit 232 and the second menu generation unit 233 separately.

The first menu generation unit 232 is configured to generate a corresponding first menu when the user attribute is the front-end user. The second menu generation unit 233 is configured to generate a corresponding second menu when the user attribute is the back-end user.

Specifically, the first menu may be a fixed menu. The fixed menu means that the function portal constituting the menu is basically unchanged, and is determined by the function or the service that the service system can provide. In this way, all function portals may be seen on the terminal device. If the registered user taps the function portal without the corresponding permission, the registered user is prompted that the permission has not been obtained.

The second menu is a dynamic menu that changes with the permission of the registered user. The dynamic menu means that the menu changes with different registered users and only some function portals are displayed on the terminal device.

To generate the dynamic menu, the second menu generation unit needs to obtain the permission of the registered user, then determine a function portal corresponding to each permission and integrate all function portals corresponding to the permission of the registered user to form a dynamic menu adaptive to the permission of the registered user.

In some other embodiments, the back-end user may be further subdivided into a system administrator and an operator.

The system administrator is a registered user who maintains the entire online diagnostic platform and operates the permission management system, and has the highest permission relative to other registered users. The operator refers to an operating manager who has a local permission and is located at the backend relative to the front-end user.

It can be understood that permissions of the front-end user and the system administrator have been determined when the entire online diagnostic platform is launched. A permission of the operator is constantly changing during use and running.

Therefore, for different registered users, the user management module 210 may be specifically configured to assign a role to the registered user when the user attribute of the registered user is the front-end user or the system administrator; and, assign one or more roles to the registered user according to the change of an actual condition when the user attribute of the registered user is the operator.

In this way, an association relationship shown in FIG. 4 may be formed: there is a one-to-one correspondence between the front-end user or the system administrator and the role. The operator may have corresponding permissions by assigning a plurality of different roles to the operator.

Still referring to FIG. 3, to prevent illegal access and restrict the registered user to access of only the authorized function, the permission management system may further include at least an execution control module 250.

The execution control module 250 is a verification module, and is configured to determine, through the menu, a function requested to be executed by the registered user; and then determine, according to the permission of the registered user, whether to execute the function requested to be executed.

That is, when the registered user has the permission, the execution control module determines to respond to the request and executes the corresponding function. When the registered user does not have the permission, the execution control module refuses to respond. Certainly, after refusing to respond, the execution control module may further display prompt information to inform the registered user that the registered user does not have the permission or inform the registered user of a possible manner of obtaining the permission.

Data, such as the role set, the permission of each role, and the storage device of the role assigned to the registered user, generated in the operation process of the foregoing function modules (such as the user management module 210, the permission management module 220 and the menu module 230) may all be stored in the database 260. Specifically, any type of database having a data retrieval function may be used.

A person skilled in the art may be further aware that, the function modules (such as the user management module 210, the permission management module 220 and the menu module 230) described in this embodiment of the present invention may be implemented by electronic hardware, computer software, or a combination thereof. To clearly describe the interchangeability between the hardware and the software, steps executed by the exemplary function modules have generally been described based on functions in the above description. Whether the functions are executed in a mode of hardware or software depends on particular applications and design constraint conditions of the technical solutions.

The described functions for each particular application may be implemented by using different methods, but it should not be considered that such implementation goes beyond the scope of the present invention. The computer software may be stored in a computer readable storage medium. When being executed, the program may include the processes of the embodiments of the foregoing methods. The storage medium may be a magnetic disk, an optical disc, a read-only memory, a random access memory, or the like.

Figure 5:
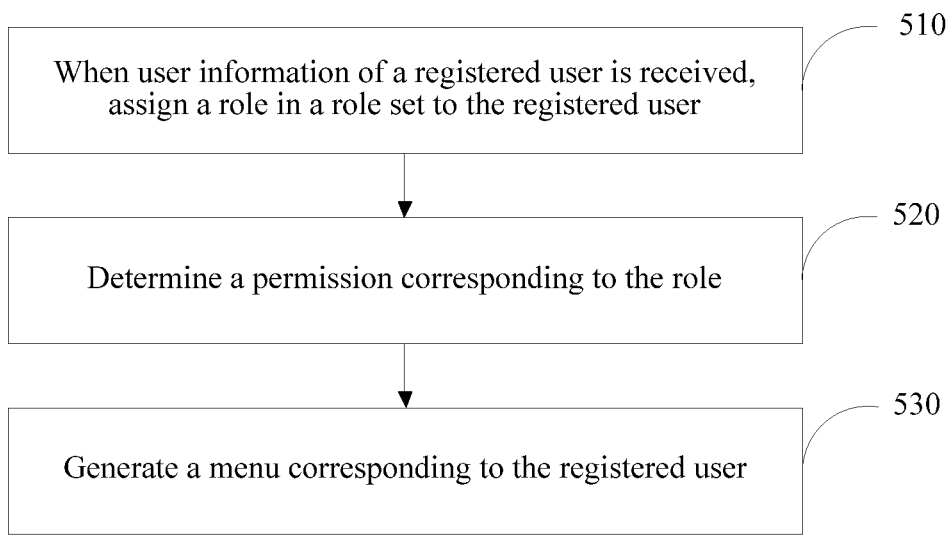
FIG. 5 is a method flowchart of a permission management method according to an embodiment of the present invention.

Based on the permission management system disclosed in the foregoing embodiments, an embodiment of the present invention further provides a permission management method. The permission management method can be applied to any type of online platform or system, thereby providing the convenience and flexibility in permission management. FIG. 5 is a method flowchart of a permission management method according to an embodiment of the present invention. As shown in FIG. 5, the permission management method includes the following steps.

510. When user information of a registered user is received, assign a role in a role set to the registered user.

The step of assigning the role may be performed when the registered user is newly created, or may be performed in the use process of the registered user. The "assign" may include: giving the role to the registered user and reducing the role owned by the registered user.

520. Determine a permission corresponding to the role.

The permission of the role may be configured by the system administrator through the online diagnostic platform according to an actual condition. The role set is a set of roles as elements. In some embodiments, in addition to creating a new role, editing operations such as deleting may be further performed on existing roles in the role set.

Specifically, to adequately meet various permission requirements of the online diagnostic platform, the permission may be a set including one or more interfaces to refine the permission to an interface hierarchy. These interfaces are functional interfaces of the service system, and may be allowed to be used by using the corresponding functions.

530. Generate a menu corresponding to the registered user. The menu includes one or more function portals.

The function portal is used for requesting execution of a diagnostic service function.

The menu refers to a set of the one or more function portals and is displayed on the terminal device through any type of interactive interface. The user may request to execute corresponding functions of the online diagnostic platform through the function portals. Generating different menus for different registered users helps meet personalized needs of different registered users.

The permission management method provides a two-layer association mode of "registered user-role-permission" to complete permission assignment and control of the online diagnostic platform, and can provide good flexibility and facilitate adaptation to function update of a service system.

Figure 6:
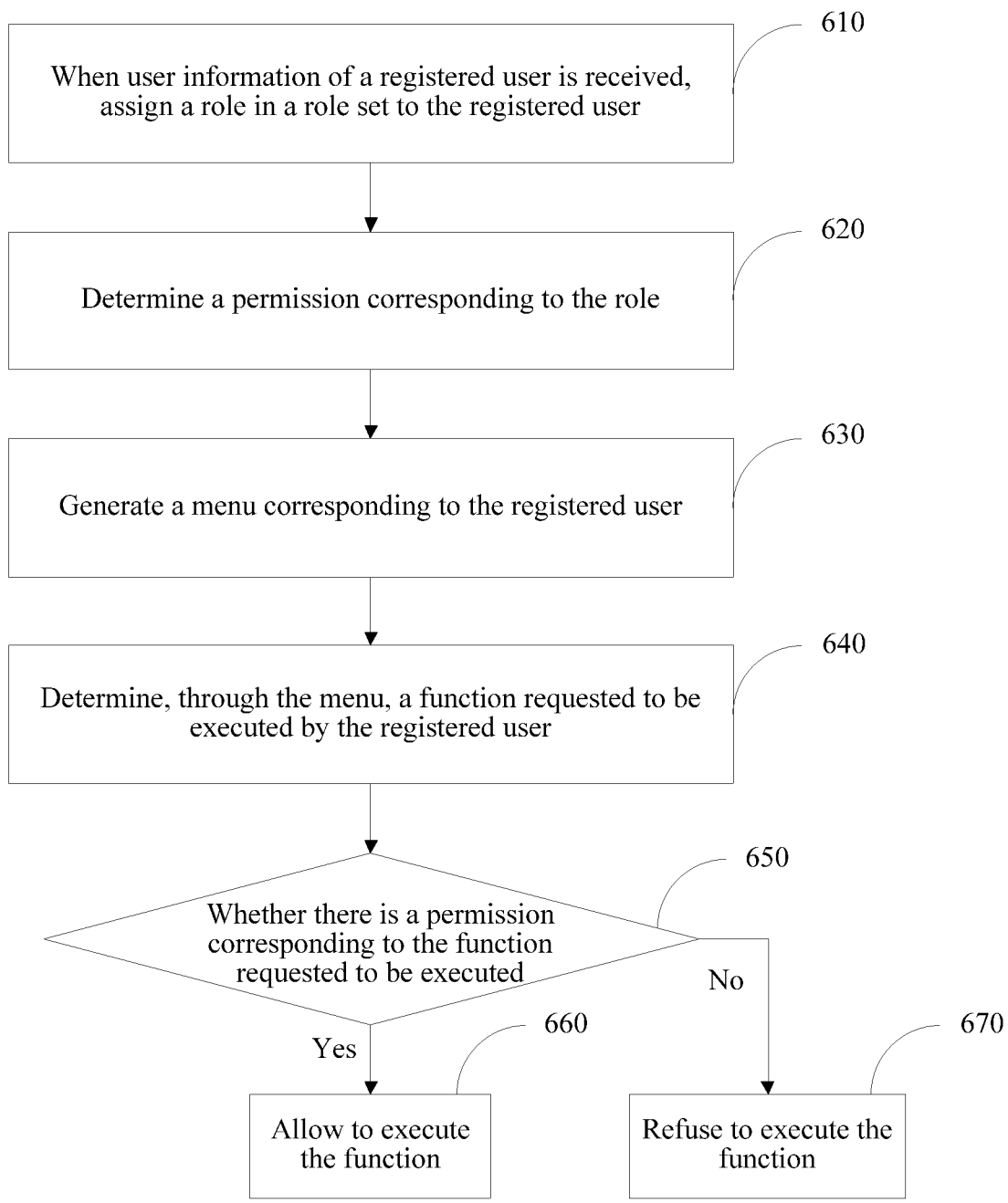
FIG. 6 is a method flowchart of a permission management method according to another embodiment of the present invention.

In the process of permission management, how to present the permission of the user to the user in a targeted manner is also a problem worth thinking about. FIG. 6 is a method flowchart of a permission management method according to another embodiment of the present invention. As shown in FIG. 6, the method includes the following steps.

610. When user information of a registered user is received, assign a role in a role set to the registered user.

620. Determine a permission corresponding to the role.

630. Generate a menu corresponding to the registered user.

Specifically, according to identities of users and use requirements, these users may be roughly classified into several different types such as a front-end user and a back-end user. Based on two different user attributes of the front-end user and the back-end user, step 630 may specifically include:

first, determining a user attribute of the registered user; and then, according to different user attributes, generating a corresponding first menu when the user attribute is the front-end user and generating a corresponding second menu when the user attribute is the back-end user.

The first menu may be a fixed menu whose function portal is unchanged. The second menu is a dynamic menu that changes with the permission of the registered user, and changes correspondingly according to different registered users.

In some embodiments, the step of generating the second menu may include the following steps: first, obtaining the permission of the registered user; then, determining a function portal corresponding to each permission; and finally, integrating all function portals corresponding to the permission of the registered user to form the second menu.

Further, the back-end user may be further subdivided into two roles of an operator and a system administrator. Based on the feature of the classification, an association relationship between the registered user and the role may be different.

A role is assigned to the registered user when the user attribute of the registered user is the front-end user or the system administrator. One or more roles are assigned to the registered user when the user attribute of the registered user is the operator.

In some other embodiments, the permission management method may further include a permission verification process for the registered user to ensure that illegal access or operations are not performed and restrict the registered user to execution of the operations only within a permission range. Still referring to FIG. 6, the verification process may include the following steps.

640. Determine, through the menu, a function requested to be executed by the registered user.

As described above, a plurality of different function portals are integrated on the menu. Therefore, the online diagnostic platform may determine, according to the function portal tapped or selected by the user, the function requested to be executed.

650. Verify whether the registered user has a permission corresponding to the function requested to be executed. If yes, perform step 660; and if no, perform step 670.

The verification may be specifically completed in any manner. For example, whether the registered user has such a permission is determined in a matching or searching manner.

660. Allow to execute the function.

When the registered user has the permission, the online diagnostic platform may provide a manner such as authority authentication or the interface, so that the online diagnostic platform may perform the function, for example, accessing a piece of data.

670. Refuse to execute the function.

When the registered user does not have the permission, the system refuses to execute the function, so as to ensure the safety of the running of the system. Certainly, the system may further publish appropriate prompt information to help the user after refusing to execute the function.

The permission management method provided in this embodiment of the present invention can prevent the illegal access or an illegal request, perform permission management on registration, restrict the registered user to access of the function only within the permission range and ensure stable running and safety of the system. In addition, the method may dynamically adjust the association relationship between different levels and has a feature of flexible configuration. The permission control is also refined to the interface hierarchy of the service system, to meet various permission requirements of users to a great extent.

Figure 7:
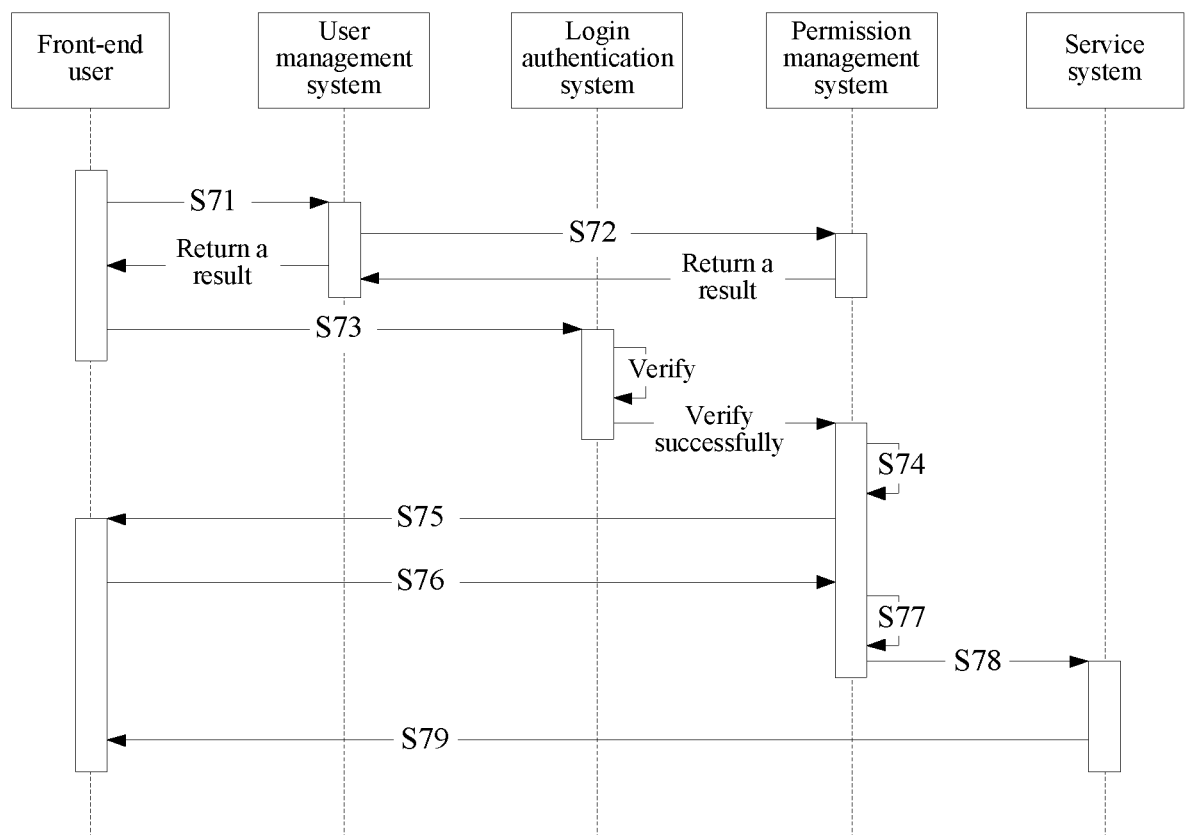
FIG. 7 is a schematic diagram of a use example of a front-end user shown in FIG. 1.
Figure 8:
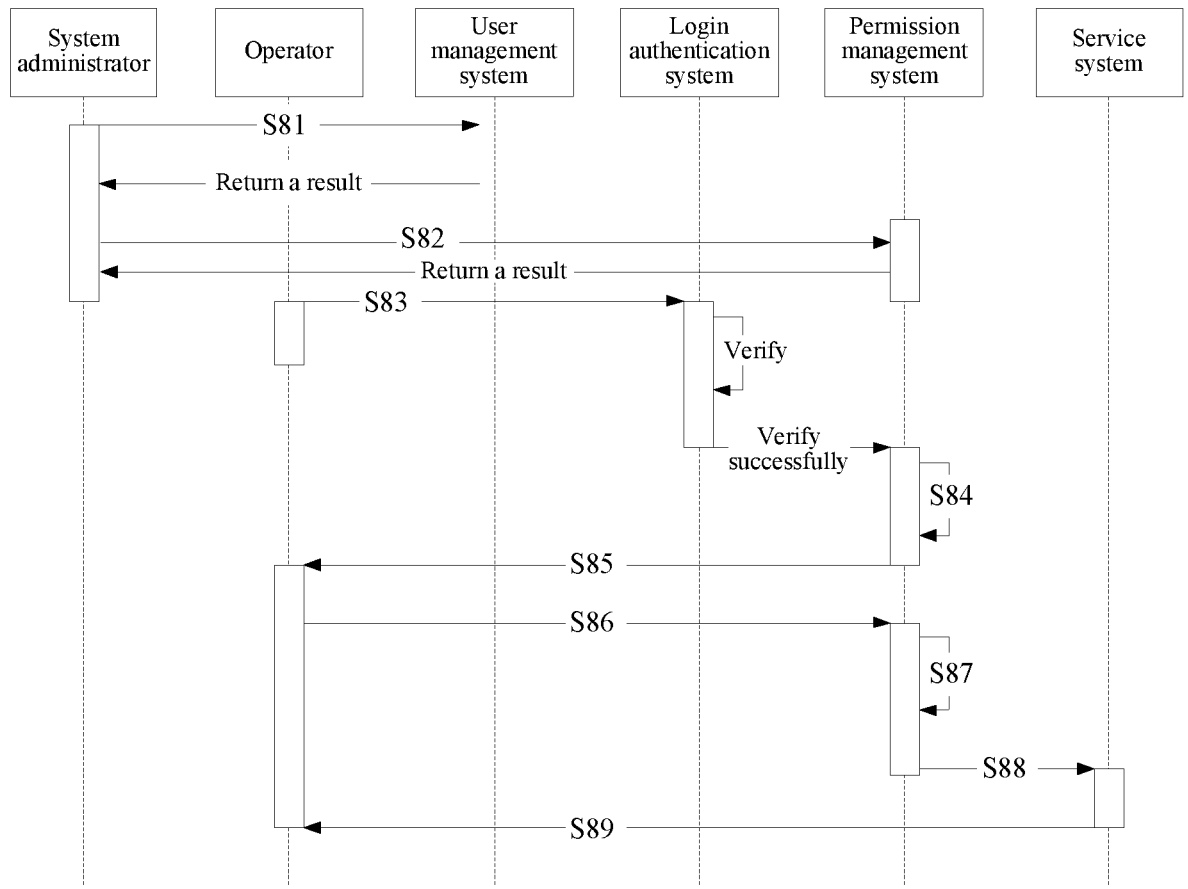
FIG. 8 is a schematic diagram of a use example of a back-end user shown in FIG. 1.

FIG. 7 and FIG. 8 are specific examples of the operation processes of the front-end user and the back-end user respectively on the online diagnostic platform shown in FIG. 1.

As shown in FIG. 7, the front-end user may create a registered user through a user management system (S71). After the registered user is successfully created, the permission management system configures a corresponding permission for the registered user by assigning a role (S72).

After the front-end user passes a login authentication system of the online diagnostic platform (S73) and is successfully verified by an account password, the permission management system executes a corresponding initialization process and loads a permission of a currently logged-in registered user (S74) to complete a login operation of the registered user (S75).

A function execution request initiated by the front-end user is determined through a function portal integrated on a fixed menu (S76). The permission management system intercepts the request and verifies whether there is a permission (S77). If there is the permission, the request is provided to a service system (S78) and an execution result of the request is returned (S79).

As shown in FIG. 8, the back-end user includes two types: a system administrator and an operator. The system administrator may create a new registered user for the operator in the user management system (S81), and operate the permission management system to configure a permission for the registered user (S82).

Then, the operator can request login of the registered user through the login authentication system (S83). After an account password is successfully verified, the permission management system executes a corresponding initialization process and loads a permission of a currently logged-in registered user (S84) to complete the login of the registered user (S85).

Similar to the process shown in FIG. 8, the operator initiates a function execution request through the function portal integrated on the dynamic menu (S86). The permission management system intercepts the request and verifies whether there is a permission (S87). If there is the permission, the request is provided to a service system (S88) and an execution result of the request is returned (S89).

Finally, it should be noted that the foregoing embodiments are merely intended for describing the technical solutions of the present invention, but not for limiting the present invention. Under the idea of the present invention, the foregoing embodiments or technical features in different embodiments may also be combined, the steps may be implemented in any order, and there are many other variations of different aspects of the present invention as described above, which are not provided in detail for brevity. Although the present invention is described in detail with reference to the foregoing embodiments, persons of ordinary skill in the art should understand that they may still make modifications to the technical solutions described in the foregoing embodiments or make equivalent replacements to some technical features thereof, without departing from the scope of the technical solutions of the embodiments of the present invention.

What is claimed is:

1. A permission management method, comprising:
when user information of a registered user is received, assigning a role in a role to the registered user;
determining a permission corresponding to the role; and
generating a menu corresponding to the registered user, wherein the menu comprises one or more function portals, the function portals being used for requesting execution of a diagnostic service function;
wherein the step of generating a menu corresponding to the registered user comprises: determining a user attribute of the registered user, wherein the user attribute comprises a front-end user and a back-end user; generating a first menu when the user attribute is the front-end user; and generating a second menu when the user attribute is the back-end user;
wherein the first menu is a fixed menu and the second menu is a dynamic menu that changes with the permission of the registered user.

2. The permission management method according to claim 1, wherein the step of generating a second menu when the user attribute is the back-end user specifically comprises:
obtaining the permission of the registered user;
determining a function portal corresponding to each permission; and
integrating all function portals corresponding to the permission of the registered user to form the second menu.

3. The permission management method according to claim 1, wherein the back-end user comprises a system administrator and an operator, and the step of assigning one or more roles in the role set to the registered user to enable the registered user to have the corresponding permission comprises:
assigning a role to the registered user when the user attribute of the registered user is the front-end user or the system administrator; and
assigning one or more roles to the registered user when the user attribute of the registered user is the operator.

4. The permission management method according to claim 1, wherein the permission is a set comprising one or more interfaces, so that a function of an online diagnostic platform corresponding to the interface is allowed to be used.

5. The permission management method according to claim 1, further comprising:
determining, through the menu, a function requested to be executed by the registered user; and
verifying whether the registered user has a permission corresponding to the function requested to be executed;
allowing to execute the function if yes; and
refusing to execute the function if no.

6. A permission management system, comprising a processor executing instructions stored in tangible memory to perform the following steps:
assigning a role in a role set to a registered user by a user management module, when user information of the registered user is received;
determining a permission corresponding to the role by a permission management module; and
generating a menu corresponding to the registered user by a menu module, wherein the menu comprises one or more function portals, the function portals being used for requesting execution of a diagnostic service function;
wherein the menu module comprises an attribute determination unit, a first menu generation unit and a second menu generation unit, and the step of generating a menu corresponding to the registered user by the menu module comprises: determining a user attribute of the registered user by the attribute determination unit, and the user attribute comprising a front-end user and a back-end user; generating a first menu by the first menu generation unit when the user attribute is the front-end user; and generating a second menu by the second menu generation unit when the user attribute is the back-end user;
wherein the first menu is a fixed menu and the second menu is a dynamic menu that changes with the permission of the registered user.

7. The permission management system according to claim 6, wherein the second menu generation unit is configured to:
obtain the permission of the registered user;
determine a function portal corresponding to each permission; and
integrate all function portals corresponding to the permission of the registered user to form the second menu.

8. The permission management system according to claim 6, wherein the back-end user comprises a system administrator and an operator, and the user management module is configured to:
assign a role to the registered user when the user attribute of the registered user is the front-end user or the system administrator; and
assign one or more roles to the registered user when the user attribute of the registered user is the operator.

9. The permission management system according to claim 6, wherein the processor executing the instructions stored in the tangible memory to further perform the following step:
adding, deleting or editing any permission by a permission editing module, and wherein each permission comprises a set of one or more interfaces, so that a function of an online diagnostic platform corresponding to the interface is allowed to be used.

10. The permission management system according to claim 6, wherein the processor executing the instructions stored in the tangible memory to further perform the following steps:
using an execution control module to: determine execution control module, through the menu, a function requested to be executed by the registered user; and determine, according to the permission of the registered user, whether to execute the function requested to be executed.

11. An online diagnostic platform, comprising:
a client, configured to receive user information of a registered user and send the user information to a permission management system, wherein the client is further configured to display menu generated by the permission management system according to the user information;
the permission management system for managing one or more registered users, wherein the permission management system is configured to:
when user information of a registered user is received, assign a role in a role set to the registered user;
determine a permission corresponding to the role; and
generate a menu corresponding to the registered user, wherein the menu comprises one or more function portals, the function portals being used for requesting execution of a diagnostic service function, wherein the menu corresponding to the registered user is generated by performing steps of: determining a user attribute of the registered user, wherein the user attribute comprises a front-end user and a back-end user; generating a first menu when the user attribute is the front-end user; and generating a second menu when the user attribute is the back-end user, wherein the first menu is a fixed menu and the second menu is a dynamic menu that changes with the permission of the registered user; and a service system, configured to execute a diagnostic service function according to a request of the client.

12. The online diagnostic platform according to claim 11, wherein the permission management system being configured to generate a second menu when the user attribute is the back-end user specifically comprises the permission management system being configured to:

obtain the permission of the registered user;

determine a function portal corresponding to each permission; and integrate all function portals corresponding to the permission of the registered user to form the second menu.

13. The online diagnostic platform according to claim 11, wherein the back-end user comprises a system administrator and an operator, and the permission management system being configured to assign one or more roles in the role set to the registered user to enable the registered user to have the corresponding permission specifically comprises the permission management system being configured to:

assign a role to the registered user when the user attribute of the registered user is the front-end user or the system administrator; and assign one or more roles to the registered user when the user attribute of the registered user is the operator.

14. The online diagnostic platform according to claim 11, wherein the permission is a set comprising one or more interfaces, so that a function of an online diagnostic platform corresponding to the interface is allowed to be used.

\* \* \* \* \*